United States Patent [19]

Wild et al.

[11] Patent Number: 5,416,209

[45] Date of Patent: May 16, 1995

[54] 5,6-DIHYDRO-DIBENZ[B,E]AZEPINE-6,11-DIONE-11-OXIMES

[75] Inventors: Hanno Wild, Wuppertal; Wolfgang Roeben, Bergisch Gladbach; Gerd Aichinger, Wuppertal; Arnold Paessens, Haan; Jörg Petersen-von Gehr, Bochum, all of Germany

[73] Assignee: Bayer Aktiengesellschaft, Leverkusen, Germany

[21] Appl. No.: 978,001

[22] Filed: Nov. 18, 1992

[30] Foreign Application Priority Data

Nov. 27, 1991 [DE] Germany ................. 41 38 853.4

[51] Int. Cl.$^6$ .................. C07D 223/20; A61K 31/55
[52] U.S. Cl. .................................................. 540/522
[58] Field of Search ......................... 540/522; 514/220

[56] References Cited

U.S. PATENT DOCUMENTS 3,431,257  3/1969  Aichinger et al. ............. 540/452
4,551,451  11/1985  Ortellin, et al. ............... 540/522

FOREIGN PATENT DOCUMENTS 0419861  4/1991  European Pat. Off. .
0429987  6/1991  European Pat. Off. .
1132516  11/1968  United Kingdom .

OTHER PUBLICATIONS

Methods in Enzymology, vol. XXXIV, "Affinity Techniques, Enzyme Purification: Part B", Bovine Trypsi and Thrombin, Hixson, Jr., and A. H. Nishikawa, pp 440–448, Academic Press, 1974.
Methods in Enzymology, vol. XXXIV, "Affinity Techniques, Enzyme Purification: Part B", Chymotrypsin(s), Tomlinson, et al., pp. 415–420, Academic Press 1974.
Affinity Chromatography, Biospecific Sorption; "Affinity Chromatography of Chymotrypsin on Soybean Trypsin Inhibitor Sepharose: Applications In Genetics And Nuclide Labelling", Gabel, Kasche, Amneus and Lundqvist, pp. 99–102, Pergamon Press, 1977.
Applied Microbiology and Biotechnology, Springer-Verlag 1979, Biotechnol. 6.; p. 195 (1979); "Recovery of Free Enzymes from Product Liquors by Bio-Affinity Adsorption: Trypsin Binding by Immobilised Soybean Inhibitor", Halling and Dunnill.
The Journal of Biological Chemistry, vol. 255, No. 15, Aug. 10, 1980, p. 7089, "Human Red Cell Purine Nucleoside Phosphorylase, Purification By Biospecific Affinity Chromatography and Physical Properties", Osborne, Mar. 17, 1980.
Hoppe-Seyler's Z. Physiol. Chem., vol. 361, p. 543, Apr. 1980, "Purification of Human and Bovine Alkaline Phosphatases by Affinity Chromatograph", Mossner, Boll and Pfleiderer.
Analytical Biochemistry, vol. 107, p. 341, (1980), "Affinity Chromatographic Sorting of Carboxypeptidase A and its Chemically Modified Derivatives", Cueni, Bazzone, Riordan & Vallee, Mar. 31, 1980.
Hoppe-Seyler's Z. Physiol. Chem., vol. 359, p. 1019, Aug. 1978, "Affinity Chromatograph of Bovine Bran β-Hexosaminidases with Substrate As Affinity ligand"., Lisman and Overdijk, May 1978.
Biochem. J. (1978), vol. 175, p. 125, "Purficiation of the Hexokinases by Affinity Chromatography on Sepharose-N-Aminoacylglucosamine Derivatives", Wright, Warsy, Holroyde and Trayer, Feb. 1978.
Archives of Biochemistry and Biophysics, vol. 198, No. 2, Dec. 1979, p. 533, "Quantitative Affinity Chromatograph of α-Chymotrpsin", Dunn and Gilbert, Aug. 10, 1979.

(List continued on next page.)

*Primary Examiner*—Nicholas Rizzo
*Attorney, Agent, or Firm*—Sprung Horn Kramer & Woods

[57] ABSTRACT

The invention relates to 5,6-dihydro-dibenz[b,e]azepine-6,11-dione-11-oximes, to processes for their preparation and to their use as inhibitors of reverse transcriptase and in particular as antiretroviral agents.

3 Claims, No Drawings

OTHER PUBLICATIONS

Understanding Enzymes, Third Ed. (Horwood Press, 1991), pp. 309–310, Trevor Palmer.
Potent And Selective Inhibition of HIV-1 Replication Invitro by A Novel Series Of TIBO Derivatives, vol. 343, Nature, Feb. 1, 1990, pp. 470–473, Rudi Pauwels, et al.
H. Mitsuya et al., 1985, Proc. Natl. Acad. Sci. USA; 82: 7096–7100.
M. A. Fischl et al., 1987, N. Engl. J. Med., 317: 187–191.
NIH State-of-the Art Conference, C. C. J. Carpenter, Panel Chair, 1990, Am. J. Med., 89: 335–344.
W. S. Saari et al., 1991, J. Med. Chem., 34: 2922–2925.
V. J. Merluzzi et al., 1990, Science, 250: 1411–1413.
E. Sandstrom et al., 1993, Drugs, 45: 637–653.
E. L. Eliel, Stereochemistry of Carbon Compounds, McGraw Hill, 1962.
Beilstein 1, 114 (1983).
Journal of Virological Methods 20, (1988), 309–321.
J. Med. Chem. 34, 2922 (1991).
J. Med. Chem. 34, 2231 (1991).
Biochemistry 30, 2022 (1991).

5,6-DIHYDRO-DIBENZ[B,E]AZEPINE-6,11-DIONE-11-OXIMES

The invention relates to 5,6-dihydro-dibenz[b,e]azepine-6,11-dione-11-oximes and to processes for their preparation.

DE 1,545,856 discloses a process for the preparation of basically substituted derivatives of 5,6-dihydrodibenz[b,e]azepine-6,11-dione-11-oxime, a few examples with aminoalkyl radicals on the oxime oxygen also being described therein.

In addition, U.S. Pat. No. 3,431,257 discloses some basically substituted 5,6-dihydro-dibenz[b,e]azepine-6,11-dione-11-oximes with psychotropic action, the compounds of the general formula (I) according to the invention partially being covered by the wording of the scope of meaning ($R^1$=alkyl) of these publications.

The present invention relates to 5,6-dihydrodibenz[b,e]azepine-6,11-dione-11-oximes of the general formula (I)

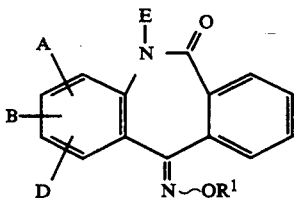

in which
A, B and D are identical or different and represent hydrogen, amino, nitro, halogen, cyano, hydroxyl, trifluoromethyl, trifluoromethoxy or straight-chain or branched alkyl or alkoxy each having up to 8 carbon atoms,
E represents hydrogen or straight-chain or branched alkyl having up to 6 carbon atoms,
$R^1$ represents hydrogen or represents cycloalkyl having 3 to 6 carbon atoms or 2-tetrahydropyranyl, represents straight-chain or branched acyl having up to 8 carbon atoms, or represents straight-chain or branched alkyl or alkenyl each having up to 10 carbon atoms, each of which is optionally substituted by halogen, hydroxyl or carboxyl, by straight-chain or branched alkoxycarbonyl having up to 6 carbon atoms or by phenyl which in turn can be substituted up to 5 times by identical or different halogen,
if appropriate in an isomeric form, and their physiologically acceptable salts.

Physiologically acceptable salts of the 5,6-dihydrodibenz[b,e]azepine-6,11-dione-11-oximes can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

The compounds according to the invention can exist in stereoisomeric forms, which either behave as image and mirror image (enantiomers), or which do not behave as image and mirror image (diastereomers). The invention relates both to the antipodes and to the racemic forms as well as to the diastereomer mixtures. The racemic forms can be separated, like the diastereomers, into the stereoisomerically uniform constituents in a known manner [cf. E. L. Eliel, Stereochemistry of Carbon Compounds, McGraw Hill, 1962].

In the radical of the general formula (II)

the C=N double bond can have either the E- or the Z-configuration, or E/Z mixtures can be present.

Preferred compounds of the general formula (I) are those in which
A, B and D are identical or different and represent hydrogen, fluorine, chlorine, hydroxyl, trifluoromethyl, trifluoromethoxy or straight-chain or branched alkyl or alkoxy each having up to 6 carbon atoms,
E represents hydrogen or straight-chain or branched alkyl having up to 4 carbon atoms,
$R^1$ represents hydrogen or represents cyclopropyl, cyclopentyl, cyclohexyl or 2-tetrahydropyranyl, or represents straight-chain or branched acyl having up to 6 carbon atoms, or represents straight-chain or branched alkyl or alkenyl each having up to 8 carbon atoms, each of which can optionally be substituted by fluorine, hydroxyl or carboxyl, by straight-chain or branched alkoxycarbonyl having up to 4 carbon atoms or by phenyl which in turn can be substituted up to 5 times by identical or different fluorine, chlorine or bromine,
if appropriate in an isomeric form, and their physiologically acceptable salts.

Particularly preferred compounds of the general formula (I) are those
in which
A, B and D are identical or different and represent hydrogen, fluorine, chlorine or straight-chain or branched alkyl or alkoxy each having up to 4 carbon atoms,
E represents hydrogen, methyl or ethyl,
$R^1$ represents hydrogen or represents cyclopropyl or 2-tetrahydropyranyl, or represents straight-chain or branched acyl having up to 4 carbon atoms, or represents straight-chain or branched alkyl or alkenyl each having up to 6 carbon atoms, each of which is optionally substituted by hydroxyl, carboxyl, fluorine, methoxycarbonyl, ethoxycarbonyl or propoxycarbonyl or by phenyl which in turn can be substituted up to 5 times by identical or different fluorine or chlorine,
if appropriate in an isomeric form, and their physiologically acceptable salts.

The compounds of the general formula (I) according to the invention can be prepared by a process in which
[A] compounds of the general formula (III)

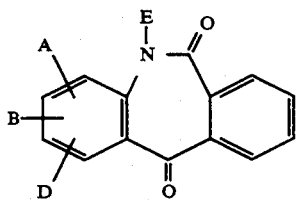

in which

A, B, D and E have the abovementioned meaning,
are reacted with hydroxylamines of the general formula (IV)

$$H_2N-OR^1 \quad (IV)$$

in which

R¹ has the abovementioned meaning,
in inert solvents, if appropriate in the presence of a base, or

[B] compounds of the general formula (Ia)

(Ia)

in which

A, B, D and E have the abovementioned meaning,
are reacted with compounds of the general formula (V)

$$L-R^2 \quad (V)$$

in which

R² has the abovementioned meaning of R¹ but does not represent hydrogen, and

L represents a typical leaving group, such as, for example, tosylate, mesylate, chlorine, bromine or iodine, likewise in inert solvents in the presence of a base, and, if appropriate, the substituents A, B, D and R¹ are varied according to customary chemical methods, and in the case in which E does not denote hydrogen, an alkylation is likewise carried out according to known methods.

The processes according to the invention can be illustrated by way of example by the following reaction scheme:

[A]

[B]

The abovementioned processes are carried out in analogy to the methods described in U.S. Pat. No. 3,431,257.

Suitable solvents for processes [A] and [B] are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Pyridine and tetrahydrofuran are preferred.

Suitable bases are the customary basic compounds. These preferably include alkali metal or alkaline earth metal hydroxides, such as lithium hydroxide, sodium hydroxide, potassium hydroxide or barium hydroxide, alkali metal hydrides such as sodium hydride, alkali metal or alkaline earth metal carbonates such as sodium carbonate or potassium carbonate, or alkali metal alkoxides such as, for example, sodium methoxide or ethoxide, potassium methoxide or ethoxide or potassium tert-butoxide, or organic amines such as benzyltrimethylammoniumhydroxide, tetrabutylammonium hydroxide, pyridine, triethylamine or N-methylpiperidine.

Processes [A] and [B] are in general carried out in a temperature range from +0° C. to +150° C., preferably from 0° C. to +120° C.

The process is in general carried out at normal pressure. However, it is also possible to carry out the process at reduced pressure or at elevated pressure (for example in a range from 0.5 to 5 bar).

Suitable solvents for the alkylation (E≠H) are likewise customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Acetone is preferred.

The alkylation is carried out in the abovementioned solvents at temperatures of 0° C. to +150° C., preferably at room temperatures up to +100° C., at normal pressure.

The compounds of the general formula (III) are known per se or can be prepared according to customary methods [cf., for example, U.S. Pat. No. 3,431,257].

The hydroxylamines of the general formula (IV) are also known or can be prepared according to known methods.

The compounds of the general formula (Ia), in the case in which E≠hydrogen, are covered by the scope of meaning of U.S. Pat. No. 3,431,257 or are new and can then be prepared by the process [A] described above.

The compounds of the general formula (V) are known [cf. Beilstein 1,114].

The inhibitors described herein are inhibitors of reverse transcriptase and can be employed as such for all purposes for which enzyme inhibitors are suitable. This is, for example, use in diagnosis in order to improve the precision and selectivity of enzyme activity measurements. In affinity chromatography, they can be used as an affinity label and in research they can be used for the elucidation of reaction mechanisms of enzymatic reactions.

Moreover, it has surprisingly been found that the compounds of the general formula (I) according to the invention have an extremely strong action against retroviruses. They show activity in lentivirus-infected cell cultures. It was possible to show this by way of the HIV virus.

HIV infection in cell culture

The HIV test was carried out with slight modifications according to the method of Pauwels et al. [cf. Journal of Virological Methods 20, (1988), 309–321].

Normal human blood lymphocytes (PBLs) were concentrated by means of Ficoll-Hypaque and stimulated with phytohaemagglutinin (90 μg/ml) and interleukin-2 (40 U/ml) in RPMI 1640 and 20% foetal calf serum. For infection with the infectious HIV, PBLs were pelleted and the cell pellet was then suspended in 1 ml of HIV virus adsorption solution and incubated for 1 hour at 37° C.

Alternatively, HIV-susceptible H9 cells were employed instead of normal human blood lymphocytes for testing the antiviral effects of the compounds according to the invention.

The virus adsorption solution was centrifuged and the infected cell pellet was taken up in growth medium so that a concentration of $1 \times 10^5$ cells per ml was established. The cells infected in this way were pipetted into the wells of 96-well microtiter plates to give $1 \times 10^4$ cells/well.

The first vertical row of the microtiter plate contained only growth medium and cells which had not been infected, but otherwise treated exactly as described above (cell control). The second vertical row of the microtiter plate contained only HIV-infected cells (virus control) in growth medium. The other wells contained the compounds according to the invention in differing concentrations, starting from the wells of the 3rd vertical row of the microtiter plate, from which the test substances were diluted $2^{10}$ times in 2-fold steps.

The test batches were incubated at 37° C. until, in the untreated virus control, the syncytia formation typical of HIV occurred (between day 3 and 6 after infection), which was then microscopically assessed. Under these test conditions, in the untreated virus control about 20–50 syncytia resulted, while the untreated cell control contained no syncytia.

The $IC_{50}$ values were determined as the concentration of the treated and infected cells at which 50% (about 10–20 syncytia) of the virus-induced syncytia were suppressed by treatment with the compound according to the invention.

It has now been found that the compounds according to the invention protect HIV-infected cells from virus-induced cell destruction.

TABLE 1:

| Ex. No. | $IC_{50}$ (μM) |
|---|---|
| 4 | 0.06 |
| 6 | 1.5 |
| 8 | 0.5 |
| 17 | 0.7 |
| 18 | 1.0 |
| 24 | 2.3 |
| 31 | 0.25 |
| (comparison) BIRG 587 [J.Med. Chem. 34 2231, (1991]] | 0.09 |

The compounds according to the invention are useful active substances in human and veterinary medicine for the treatment and prophylaxis of diseases caused by retroviruses.

Indication areas in human medicine which can be mentioned are, for example:

1.) The treatment and prophylaxis of human retrovirus infections.
2.) For the treatment or prophylaxis of diseases (AIDS) caused by HIV I (human immunodeficiency virus; formally called HTLV III/LAV) and HIV II and the stages associated therewith such as ARC (AIDS-related complex) and LAS (lymphadenopathy syndrome) and also the immunodeficiency and encephalopathy caused by this virus.
3.) For the treatment or the prophylaxis of an HTLV-I or HTLV-II infection.
4.) For the treatment or the prophylaxis of the AIDS-carrier state (AIDS-transmitter state).

Indications in veterinary medicine which can be mentioned are, for example:
Infections with
a) Maedivisna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by feline leukaemia virus
g) infections caused by feline immunodeficiency virus (FIV)
h) infections caused by simian immunodeficiency virus (SIV)

The abovementioned items 2, 3 and 4 are preferred from the indication area in human medicine.

The present invention includes pharmaceutical preparations which, in addition to non-toxic, inert pharmaceutically suitable excipients, contain one or more compounds of the formula (I) or which consist of one or more active substances of the formula (I), and processes for the production of these preparations.

The active substances of the formula (I) should preferably be present in the abovementioned pharmaceutical preparations in a concentration of about 0.1 to 99.5% by weight, preferably of about 0.5 to 95% by weight, of the total mixture.

Apart from the compounds of the formula (I), the abovementioned pharmaceutical preparations can also contain other pharmaceutical active substances.

The abovementioned pharmaceutical preparations are prepared in a customary manner by known methods, for example by mixing the active substance or substances with the excipient or excipients.

In general, it has proved advantageous both in human and in veterinary medicine to administer the active substance or substances according to the invention in total amounts of about 0.1 to about 200 mg/kg, preferably 1 to 100 mg/kg, of body weight every 24 hours, if appropriate in the form of several individual doses, to achieve the desired results. An individual dose contains the active substance or substances preferably in amounts of about 1 to about 80, in particular 1 to 30, mg/kg of body weight. However, it may be necessary to depart from the dosages mentioned, in particular depending on the nature and the body weight of the subject to be treated, the type and the severity of the disease, the type of preparation and the administration of the medicament as well as the time or interval within which administration takes place.

PREPARATION EXAMPLES

Example 1

(E/Z)-2-Chloro-11-hydroxyimino-6-oxo-5,6-dihydro-11-H-dibenz[b,e]azepine

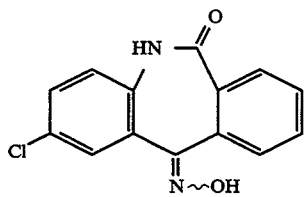

10 g (39 mmol) of 2-chloro-6,11-dioxo-5,6-dihydro-11H-dibenz[b,e]azepine and 3.24 g (46 mmol) of hydroxylamine hydrochloride in 80 ml of pyridine are heated at 100° C. for 18 h. The mixture is then poured into 2N hydrochloric acid and the precipitated product is filtered off. Recrystallisation from ethanol yields 9.23 g of the oxime.

Example 2

(E/Z)-11-tert-Butoxyimino-2-chloro-6-oxo-5,6-dihydro-11-H-dibenz [b,e]azepine

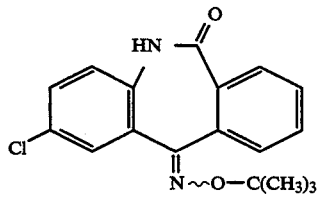

0.5 g (2.2 mmol) of 2-chloro-6,11-dioxo-5,6-dihydro-11-H-dibenz[b,e]azepine and 304 mg (2.4 mmol) of O-tert-butylhydroxylamine in 4.4 ml of pyridine are heated at 100° C. for 6 h. The mixture is then poured into 2 N hydrochloric acid and the precipitated product is filtered off. Recrystallisation from ethanol/water yields 307 mg of product.

$^1$H-NMR (DMSO): $\delta=1.30$ and 1.31 (2s, 9H); 7.20 and 7.25 (2d, J=9 Hz, 1H); 7.35–7.8 (m, 5H); 7.9 (m, 1H); 10.68 and 10.74 (2s, NH).

Example 3

(E/Z)-2-Chloro-11-isopropoxyimino-6-oxo-5,6-dihydro-11-H-dibenz[b,e]azepine

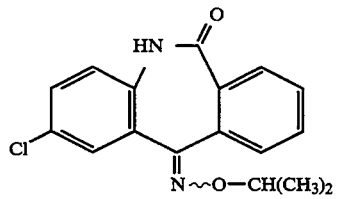

300 mg (1.1 mmol) of (E/Z)-2-chloro-11-hydroxyimino-6-oxo-5,6-dihydro-11H-dibenz[b,e]azepine in 2.2 ml of abs. THF are treated with 36.3 mg (1.2 mmol) of an 80% strength suspension of NaH in oil and heated under reflux for 30 min. 121 μl (1.21 mmol) of 2-iodopropane are added and the mixture is heated under reflux for a further 18 h. It is then filtered, the filtrate is concentrated and the residue is purified on silica gel using CH$_2$Cl$_2$/EtOAc 10:1.

Yield: 125 mg $^1$H-NMR (CDCl$_3$): $\delta=1.23$ and 1.28 (2d, J=6 Hz, 3H); 1.32 and 1.36 (2d, J=6 Hz, 3H); 4.50 and 4.52 (2 septet, J=6 Hz, 1H); 7.05 and 7.10 (2d, J=9 Hz, 1H); 7.28 (m, 1H); 7.48–7.65 (m, 4H); 8.08 (d, J=9 Hz, 1H); 9.08 and 9.12 (2s, NH).

Example 4

(E)-2-Chloro-11-ethoxyimino-6-oxo-5,6-dihydro-11-H-dibenz [b,e]azepine

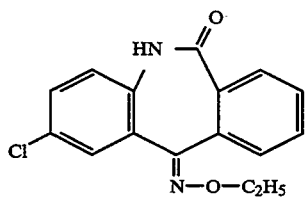

(E/Z)-2-Chloro-11-hydroxyimino-6-oxo-5,6-dihydro-11-H-dibenz[b,e]azepine is separated into the pure (E) and (Z) components by HPLC on an Si60 phase and 3% isopropanol in petroleum ether. 50 mg (0.18mmol) of the (E) compound in 0.18 ml of ethanol and 0.54 ml of THF are treated at 0° C. with 71 mg (0.27 mmol) of triphenylphosphane and then with a solution of 56 μl (0.36 mmol) of diethyl azodicarboxylate in 0.18 ml of ethanol. The mixture is stirred overnight at room temperature and evaporated and the residue is purified on silica gel using CH$_2$Cl$_2$/EtOAc 30:1.

Yield: 29 mg $^1$H-NMR (CDCl$_3$): $\delta=1.30$ (t, J=6 Hz, 3H); 4.26 (m, 2H); 7.00 (d, J=8 Hz, 1H); 7.30 (m, 1H); 7.45–7.70 (m, 4H); 8.08 (d, J=8 Hz, 1H); 8.61 (s, NH).

The examples shown in Table 1 are prepared in analogy to the procedures of Examples 1–4:

TABLE 1

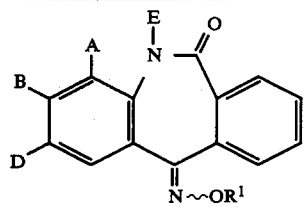

| Ex. No. | A | B | D | E | R[1] | E/Z | analogous to Example |
|---|---|---|---|---|---|---|---|
| 5 | H | H | H | H | —CH$_3$ | 1:1 | 2 |
| 6 | H | H | —Cl | H | —CH$_3$ | 1:1 | 2 |
| 7 | H | H | —Cl | —CH$_3$ | —CH$_3$ | 1:1 | 2 |
| 8 | H | H | —Cl | H | —C$_2$H$_5$ | Z | 4 |
| 9 | H | H | H | H | —C$_2$H$_5$ | 1:1 | 2 |
| 10 | Cl | H | H | H | —C$_2$H$_5$ | 1:1 | 2 |
| 11 | —CH$_3$ | H | H | H | —C$_2$H$_5$ | 1:1 | 2 |
| 12 | H | —CH$_3$ | H | H | —C$_2$H$_5$ | 1:1 | 2 |
| 13 | H | H | —CH$_3$ | H | —C$_2$H$_5$ | 1:1 | 2 |
| 14 | H | H | —Cl | H | —C$_3$H$_7$ | 1:1 | 3 |
| 15 | H | H | —Cl | H | cyclopropyl | 1:1 | 2 |
| 16 | H | H | —Cl | H | —CH$_2$—CH=CH$_2$ | 1:1 | 2 |
| 17 | H | H | —Cl | H | —CH$_2$C$_6$H$_5$ | 1:1 | 2 |
| 18 | H | H | —Cl | H | —CH$_2$-C$_6$F$_5$ | 1:1 | 2 |
| 19 | H | H | —Cl | H | —CH$_2$-(2,6-Cl$_2$C$_6$H$_3$) | 1:1 | 2 |
| 20 | H | H | H | H | —CH$_2$CO$_2$H | 1:1 | 2 |
| 21 | H | H | —Cl | H | —CH$_2$CO$_2$H | 1:1 | 2 |
| 22 | H | H | H | H | —CH$_2$CO$_2$CH$_3$ | 1:1 | 2 |
| 23 | H | H | H | H | —CH$_2$CO$_2$CH$_3$ | Z | 4 |
| 24 | H | H | —Cl | H | —CH$_2$CO$_2$CH$_3$ | 1:1 | 2 |
| 25 | H | H | —Cl | H | —CH$_2$CO$_2$CH$_3$ | Z | 4 |
| 26 | H | H | —Cl | —CH$_3$ | —CH$_2$CO$_2$CH$_3$ | 1:1 | 2 |
| 27 | H | H | H | H | —CH$_2$CO$_2$C$_2$H$_5$ | 1:1 | 2 |
| 28 | H | H | —Cl | H | —CH$_2$—CO$_2$C$_2$H$_5$ | 1:1 | 2 |
| 29 | H | H | —Cl | —CH$_3$ | —CH$_2$—CO$_2$C$_2$H$_5$ | 1:1 | 2 |
| 30 | H | H | —Cl | H | —(CH$_2$)$_4$CO$_2$C$_2$H$_5$ | 1:Z | 2 |
| 31 | H | H | —Cl | H | tetrahydropyran-2-yl | 1:1 | 2 |
| 32 | H | H | —Cl | H | —(CH$_2$)$_2$OH | 1:1 | 2 |
| 33 | H | H | —Cl | H | —CO—CH$_3$ | 1:1 | 2 |
| 34 | H | H | —Cl | H | —CH(CH$_3$)$_2$ | Z | 4 |

TABLE 1-continued

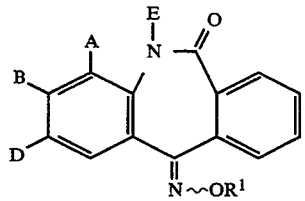

| Ex. No. | A | B | D | E | R¹ | E/Z | analogous to Example |
|---|---|---|---|---|---|---|---|
| 35 | H | H | —Cl | H | .CH(CH₃)₂ | E | 4 |

We claim:
1. 5,6-Dihydro-dibenz[b,e]azepine-6,11-dione-11-oximes of the formula (I):

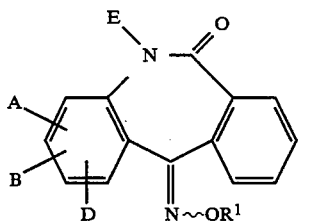

in which
A, B and D are indentical or different and represent hydrogen, amino, nitro, halogen, cyano, hydroxyl, trifluoromethyl, trifluoromethoxy or straight-chain or branched alkyl or alkoxy each having up to 8 carbon atoms;
E represents hydrogen or staight-chain or branched alkyl having up to 6 carbon atoms; and
R¹ represents cycloalkyl having 3 to 6 carbon atoms; or
represents 2-tetrahydropyranyl; or
represents straight-chain or branched acyl having up to 8 carbon atoms; or
represents straight-chain or branched alkyl having up to 10 carbon atoms which is substituted by halogen, hydroxyl, carboxyl, straight-chain or branched alkoxycarbonyl having up to 6 carbon atoms, or by phenyl which is optionally substituted up to 5 times by identical or different halogen atoms; or
represents straight-chain or branched alkenyl having up to 10 carbon atoms which is optionally substituted by halogen, hydroxyl, carboxyl, straight-chain or branched alkoxycarbonyl having up to 6 carbon atoms, or by phenyl which is optionally substituted up to 5 times by identical or different halogen atoms;
if appropriate in an isomeric form, or a physiologically acceptable salt thereof.
2. A compound according to claim 1, wherein such compound is selected from the group consisting of:

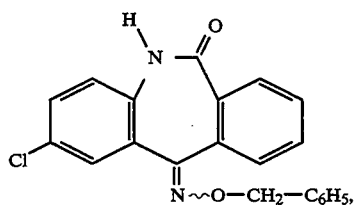

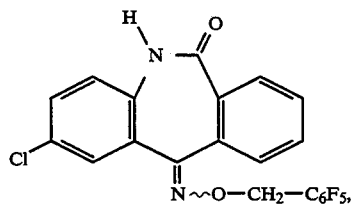

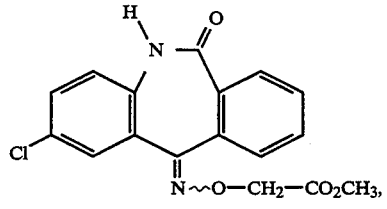

and

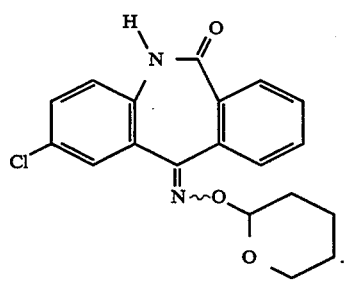

3. 5,6-Dihydro-dibenz[b,e]azepine-6,11-dione-11-oximes of the formula (I):

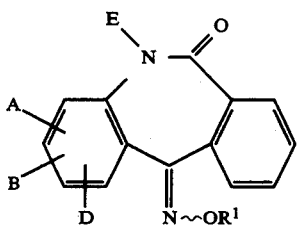

(I)

in which
A, B and D are indentical or different and represent amino, nitro, cyano, hydroxyl, trifluoromethyl or trifluoromethoxy;
E represents hydrogen or staight-chain or branched alkyl having up to 6 carbon atoms; and
$R^1$ represents hydrogen; or
represents cycloalkyl having 3 to 6 carbon atoms; or
represents 2-tetrahydropyranyl; or
represents straight-chain or branched acyl having up to 8 carbon atoms; or
represents straight chain or branched alkyl having up to 10 carbon atoms which is optionally substituted by halogen, hydroxyl, carboxyl, straight-chain or branched alkoxycarbonyl having up to 6 carbon atoms, or by phenyl which is optionally substituted up to 5 times by identical or different halogen atoms; or
represents straight-chain or branched alkenyl having up to 10 carbon atoms which is optionally substituted by halogen, hydroxyl, carboxyl, straight-chain or branched alkoxycarbonyl having up to 6 carbon atoms, or by phenyl which is optionally substituted up to 5 times by identical or different halogen atoms;
if appropriate in an isomeric form, or a physiologically acceptable salt thereof.

* * * * *